United States Patent [19]

Byrom et al.

[11] Patent Number: 5,519,130
[45] Date of Patent: May 21, 1996

[54] PURIFICATION PROCESS BY DECOMPOSITION OF HALOALKANOLIC ACID WITH DEHALOGENASE

[75] Inventors: David Byrom, Middlesbrough; Barbara A. Abbishaw, Sherbourne Hill, both of United Kingdom

[73] Assignee: Zeneca Limited, London, England

[21] Appl. No.: 307,757

[22] PCT Filed: Mar. 26, 1993

[86] PCT No.: PCT/GB93/00628

§ 371 Date: Nov. 21, 1994

§ 102(e) Date: Nov. 21, 1994

[87] PCT Pub. No.: WO93/20223

PCT Pub. Date: Oct. 14, 1993

[30] Foreign Application Priority Data

Mar. 27, 1992 [GB] United Kingdom ............... 920667

[51] Int. Cl.$^6$ ............... C08B 11/20; C08G 65/32; C12P 7/42; C07C 323/52
[52] U.S. Cl. ............... 536/85; 435/128; 435/129; 435/130; 435/132; 435/135; 435/195; 435/262; 435/264; 252/174.12; 252/174.21; 252/174.22; 252/183.11; 252/DIG. 1; 536/76; 536/82; 536/98; 562/512

[58] Field of Search ............... 536/85, 76, 82, 536/98; 435/130, 128, 132, 135, 262, 129, 264, 195; 252/174.21, 174.22, 174.12, 183.11, DIG. 1

[56] References Cited

U.S. PATENT DOCUMENTS

| 4,804,629 | 2/1989 | Roy | 435/262 |
| 5,322,782 | 6/1994 | Nakajima et al. | 435/195 |
| 5,372,944 | 12/1994 | Swanson | 435/262 |

FOREIGN PATENT DOCUMENTS 179603  3/1993  European Pat. Off. .

*Primary Examiner*—Herbert J. Lilling
*Attorney, Agent, or Firm*—Cushman Darby & Cushman

[57] ABSTRACT

Haloalkanoic acid impurities are decomposed in the presence of certain surfactants carboxymethyl cellulose or thioglycollic acids salts which may contain them as unconverted reactants by contacting them with dehalogenase enzyme.

10 Claims, No Drawings

PURIFICATION PROCESS BY DECOMPOSITION OF HALOALKANOLIC ACID WITH DEHALOGENASE

THIS INVENTION relates to a purification process.

In industrial processes materials may be encountered which contain unwanted haloalkanoic acids which contain 2 to 6 for example 2 to 4 carbon atoms or amides or esters thereof in which at least one carbon atom especially the α-carbon atom is bound to a halogen, especially chlorine, atom, which materials preferably contain only one halogen atom (herein referred to as HAAs), for example chloroacetic acid.

We have found that dehalogenase enzymes, especially those derived from Pseudomonas are remarkably effective in decomposing such substances in the presence of high concentrations of carboxymethyl cellulose, surface active agents and thioglycollic acid salts, in for example concentrations of 5%, 10% or more for example. 50% or more in water, all percentages being by weight.

Certain surface active agents (surfactants) are made by processes which comprise reacting active hydrogen atoms with haloalkanoic acids or esters or amides thereof as aforesaid. Such surface active agents may comprise carboxy alkyl groups or esters or amides thereof, for example groups of formula $R(AO)_n OZCOOH$ in which R is an alkyl phenyl or preferably alkyl group containing 8 to 20 and preferably 9 to 18 carbon atoms, n has a value of 1 to 20 and preferably 1½ to 20 and is preferably 2 to 12 and represents an average value, AO is one or more alkylene oxide groups which preferably comprise ethylene and/or propylene oxide groups and may consist essentially of such groups, and Z is an alkylene group having 1 to 4 carbon atoms, for example a $CH_2$ group. Residues of the HAAs may remain in the product as an impurity however and it may be desired to remove them.

The invention comprises a process in which free haloalkanoic acids or esters or amides thereof as aforesaid are decomposed in the presence of a surfactant which comprises a carboxyalkyl group or an ester or amide thereof, carboxymethyl cellulose or of a thioglycollic acid salt by contacting it with a dehalogenase enzyme which may be a dehydrohalogenase enzyme.

The process is suitably carried out at a pH of 6 to 9 the temperature is suitably 15°–40° C.

Sufficient enzyme is preferably present to enable the process to be completed within two days. The rate may be increased by increasing the quantity of enzyme present, and the process may be completed more rapidly by this means.

The invention also comprises a process of producing a surfactant a thioglycollic acid salt or carboxymethyl cellulose which comprises reacting a substance having reactive hydrogen atoms with a haloalkanoic acid to form a carboxyalkyl derivative thereof and decomposing residual haloalkanoic acid in the product by contacting the product with a dehydrohalogenase enzyme.

If desired, small quantities of enzyme may be added to the relevant products before they are distributed and the decomposition of haloalkanoic acid may proceed during transport or storage of the product.

The enzyme may be produced using a bacterium which may belong to any genus but is suitably a strain of Pseudomonas, especially a strain of the species *Pseudomonas putida* or *Pseudomonas fluorescens*, preferably *Pseudomonas putida* NCIMB 12018.

5 stains of bacteria which can be used as sources from which the enzyme composition may be isolated have been deposited at the National Collection of Industrial and Marine Bacteria, PO Box 31, 135 Abbey Road, Aberdeen, Scotland, UK, and have been assigned the following accession numbers:

|   |   |   | Deposited |
|---|---|---|---|
| 1 | *Pseudomonas putida* | NCIMB 12018 | 20.09.1984 |
| 2 | *Pseudomonas fluorescens* | NCIMB 12159 | 30.09.1985 |
| 3 | NCIB 12160 | | 30.09.1985 |
| 4 | NCIB 12161 | | 30.09.1985 |
| 5 | *Pseudomonas putida* | NCIB 12158 | 30.09.1985 |

The enzyme may be isolated from bacteria, for example *P. putida* NCIB 12018, by techniques well known on the enzyme art, e.g. absorption, elution, and precipitation techniques. For example, cells of a suitable organism may be ruptured, for example in a French pressure cell. The homogenate suspension may be separated into a solid phase and a liquid phase by conventional biochemical separation methods, e.g. centrifugation or filtration, and a cell-free extract in a suitable buffer may be obtained. Suitable buffers include inter alia phosphate, trishydroxymethyl-aminomethane ("Tris"), bicarbonate, glycine, imidazole, etc. The concentration of the buffer solution is typically between 1 mM and 200 mM, e.g. about 25 mM.

The cell-free extract may be fractioned using fractionating techniques which are capable of separating molecules according to inter alia their molecular size and/or charge, for example, ultrafiltration, electrophoresis, e.g. on a polyacrylamide gel, or chromatography, e.g. on a DEAE-Sephacel column. Identification of the appropriate fraction and the isolation therefrom of the enzyme having the desired enzymatic activity may be carried out using techniques known in the art, for example those described by Weightman et al, Journal of General Microbiology, 1980, Volume 121, pages 187–193.

The process according to the present invention may be carried out using an intra- or extra- cellular enzyme. Where an extra-cellular enzyme Ks used it may be in an "immobilised" or "insolubilised" form. Where an intra-cellular enzyme is used the cells may be in an "immobilised" or "insolubilised" form.

Techniques are known in the art to "immobilise" or "insolubilise" enzymes and cells by suitable known treatment, e.g. flocculation, or by physically or chemically coupling them to essentially insoluble, inert carrier materials, thus facilitating their use in flow through reactors. As used herein the terms "immobilised enzyme" and "immobilised cell" mean an enzyme or cell which is physically or chemically bonded to or entrapped in an insoluble carrier material or has been treated to form an insoluble mass, e.g. flocculated. When the immobilised enzyme is contacted with a liquid in which it is normally soluble, the enzyme remains attached to the carrier material. Where immobilised cells are contacted with a liquid in which the cells are normally readily dispersible the cells remain attached to the carrier material or as a flocculated mass.

Various materials may be used for the carrier. For example, enzymes and cells may be bonded to various organic materials, e.g. various cellulose derivatives, polyamino-styrene beds, etc., or to various inorganic materials, e.g. porous glass and silica gels. Methods for absorbing enzymes to silicous materials are described in U.S. Pat. No. 3,556,945. Inorganic materials, more preferably alkali-resistant ceramics, are preferred.

Techniques for entrapping enzymes and cells in suitable insoluble carrier materials such as gels, e.g. polyacrylamide or carrageenan, or for flocculating them are well known in the art (Burke, Philosophical Transactions of the Royal Society of London, 1983, Volume 300, pages 369–389; Mosback, Structure and Order in Polymers Lecture International Symposium 1980, Pergammon 1981, Pages 231–238).

Where intra-cellular enzymes are used suitable cells may be prepared by, for example, mutation or genetic engineering. The mutation treatment may comprise a physical treatment, e.g. exposure to suitable electro magnetic radiation such as UV light, or a chemical treatment with a suitable chemical e.g. N-methyl-$N^1$-nitro-N-nitrosoguanidine. Suitable chemical treatments include those described by Ornston (Journal of Biological Chemistry, Volume 241, pages 3800–3810).

Alternatively, genetic information which codes for the enzyme may be transferred from a microorganism in which it occurs naturally, preferably *Pseudomonas putida* or *fluorescens* to a suitable foreign organism, i.e. an organism in which it does not naturally occur. For example, a plasmid, on which the genes coding for D-2-Haloalkanoic acid (HAA) HAA-halidohydrolase may be carried (Kawasaki et al, Agricultural and Biological Chemistry, 1981, Vol 45, pages 29–34) may be isolated by known techniques, e.g. a salt precipitation technique (Guerry et al, Journal of Bacteriology, 1973, Volume 116, pages 1064–1066), and may be further purified by known techniques, e.g. by cesium chloride-ethidium bromide density gradient centrifugation. The gene may be introduced into the foreign organism by known methods, e.g. transformation. Alternatively, the gene may be transferred directly to a second organism by, for example, cell conjugation, which process may require mobilisation (Beaching et al, J. Gen. Microbiol., 1983, Vol. 129, pages 2071 to 2078).

As examples of suitable foreign organisms which, it will be appreciated, do not adversely affect production of the enzyme nor react adversely, may be mentioned inter alia, *Escherichia coli, Methylophilus methylotrophus* (particularly the strains NCIB Nos. 10508 to 10515 and 10592 to 10596 which are described in our UK Patent Specification No. 1370892) and *Bacillus subtilis*.

Cells of a suitable organism may be grown in a conventional growth medium by a continuous, batch or fed-batch technique. The growth medium typically comprises an aqueous mineral salts solution and a suitable carbon source e.g. glucose, ethanol, acetic acid or 2-HAA. The concentration of the carbon source can vary over a wide range but is generally between 1% (w/v) and 5% (w/v). Oxygen or an oxygen containing gas, must be present during the growth period. The temperature of the medium during the growth period may vary considerably but normally will be in the range of 25° C. to 35° C. The pH of the medium is kept within the range of t.t to 8.0 during growth and preferably at 6.5 to 7.5. The size of the culture can vary considerably for example between 1.5 and 50,000 liters.

The process may be carried out in a substantially oxygen-free atmosphere since we have found that under reduced oxygen tension the half-life of the enzyme is increased. Preferably the process is carried out in a nitrogen atmosphere.

EXAMPLE

The base sequence corresponding to a known active enzyme derived from *Pseudomonas putida* AJ1 which is deposited as NCIMB 12018 with National Collection of Industrial and Marine Bacteria, PO Box 31, 135 Abbey Road, Aberdeen, Scotland, UK has been published by Barth, Bolton & Thompson, Journal of Bacteriology 174 (8) 1992, pages 2612–2619.

A bacterium which was a *P. putida* transconjugant containing non conjugative plasmids encoding the dehalogenase gene sequence which had been mobilised from E coli by RP4 produced according to the Materials and Methods Section of the said paper by Barth, Bolton and Thompson, which is incorporated herein by reference was treated as follows:

dehalogenase Enzyme Production
3L of a medium 'A' containing per liter of water

| | |
|---|---|
| $MgSO_4 \cdot 7H_2O$ | 2.5 g |
| $K_2SO_4$ | 1.6 g |
| $H_3PO_4$ | 4.3 g |
| $Ca^{2+}$ | 54 mg |
| $Zn^{2+}$ | 1.7 mg |
| $Mn^{2+}$ | 1.9 mg |
| $Cu^{2+}$ | 0.38 mg |
| $Fe^{2+}$ | 10 mg |
| Glucose | 20 g |
| PPG Antifoam | 0.3 ml | is inoculated with a small shake flask containing the said strain of *Pseudomonas putida*. Temperature is controlled at 28° C., pH is controlled at 6.9. The taxonomy of *Pseudomonas putida* and *Pseudomonas fluorescens* have been described in Bergey's Manual of Systematic Bacteriology Volume 1, copyright 1984.

When glucose depletion occurs, fully continuous operation proceeds at a dilution rate of 0.1 $h^{-1}$–0.15 $h^{-1}$. Feed concentration to the fermenter during continuous operation, per liter of water, is as follows:

| | |
|---|---|
| $MgSO_4 \cdot 7H_2O$ | 1.6 g |
| $K_2SO_4$ | 1.0 g |
| $H_3PO_4$ | 1.0 g |
| $Ca^{2+}$ | 33 mg |
| $Zn^{2+}$ | 1.1 mg |
| $Mn^{2+}$ | 1.2 mg |
| $Cu^{2+}$ | 0.24 mg |
| $Fe^{2+}$ | 18.6 mg |
| Glucose | 94 g |
| PPG Antifoam | 1.5 ml |
| SMCA (Sodium monochloroacetate) | 2.3 g |

Temperature is controlled at 28° C., pH at 6.9, chloroacetic acid sodium salt (20 mMolar) (SMCA) is used as an enzyme inducer.

Harvesting

Fermenter culture is collected and concentrated up to approximately 120 g/l Dry Cell Weight (DCW). It is then spray dried, at an inlet temperature of 200° C., and outlet temperature of 100° C. A dried particle size range of 12–30 micron is achieved under these drying conditions, with little enzyme degradation. By this means a composition comprising the aforesaid enzyme was produced.

Preparation of surfactants prior to addition of enzyme preparation:

Sample 1

12 gms of a surfactant of the following composition, 65% $R(EO)_{2\frac{1}{2}}COOH + 20\% R(EO)_{2\frac{1}{2}}OH$ in which EO represents molecules of ethylene oxide was added to 88 mls of 100 mMolar potassium phosphate buffer pH 7.2. The pH of the resulting solution was adjusted to 7.2 using 5 molar sodium hydroxide.

Sample 2

10 gms of a surfactant of the following composition, 90% $R(EO)_7CH_2COOH$ in water, was added to 90 mls of 100 mMolar potassium phosphate buffer pH 8.2. The pH of the resulting solution was adjusted to 7.2 using 5 molar sodium hydroxide.

In both samples the group R was a mixture of $C_{13}$ and $C_{15}$ alkyl groups, and the number of EO groups was an average. Unreacted chloroalkanoic acid (chloropropionic and chloroacetic acid respectively) was present.

Preparation of Catalyst Suspension 10 gms dry weight of spray dried cells was resuspended in 100 mls of 100 mMolar potassium phosphate buffer of pH 7.2. The resulting cell suspension had an activity of 40 specific activity units/ml. Units of specific activity are defined as the milli moles chloride released/hour/gram dry weight of cells at an incubation temperature of 28° C.

Chloroalkanoic Acid Decomposition 1 ml of the above cell suspension containing 40 units of activity was added to 50 mls of each of the prepared neutralised solutions of surfactants in a 100 ml sealable beaker.

A magnetic bar was added to each container and these were then placed on a magnetic stirrer to provide agitation. These were incubated at 28° C.

At various time intervals, between time 0 and 48 hours samples were removed and free chloride estimated.

Reaction rate and completion were monitored using this technique.

Estimation of Chloride Ion Concentration

A standard analytical technique was used which involves potentiometric titration of free chloride with a silver nitrate solution.

Experimental Results Obtained

| Time hrs/sample | Sample 1 Chloride Ions gms/litre | Sample 2 of Chloride Ions gms/litre |
|---|---|---|
| 0 | 0.306 | 0.20 |
| 24 | 0.714 | 0.252 |

The increase in chloride ions is indicative of the dechlorination of residual chloroalkanoic acid.

We claim:

1. A process in which a free haloalkanoic acid is decomposed in the presence of a surfactant which comprises a carboxyalkyl group or an ester or amine thereof, carboxymethyl cellulose or a thioglycollic acid salt by contacting said haloalkanoic acid with a dehalogenase enzyme, wherein said haloalkanoic acid is chloroacetic acid or chloropropionic acid.

2. A process as claimed in claim 1 in which the surfactant is of formula R(AO)n OZCOOH in which R is an alkylphenyl or alkyl group having 8 to 20 carbon atoms, n has a value of 1½ to 20, AO is an alkylene oxide residue, n is an average value and Z is an alkylene group having 1 to 4 carbon atoms.

3. A process as claimed in claim 1 in which the pH is 6 to 9 and the temperature is 15° to 40° C.

4. A process as claimed in claim 1 which is carried out at a concentration of 5% or more of carboxymethyl cellulose, thioglycollic acid salt or surface active agent in water.

5. In a process of producing a surfactant, thioglycollic acid salt or carboxymethyl cellulose which comprises reacting a substance having reactive hydrogen atoms with a haloalkanoic acid to form a carboxyalkyl derivative thereof, wherein said haloalkanoic acid is chloroacetic acid or chloropropionic acid, wherein the improvement comprises decomposing residual haloalkanoic acid in the product by contacting it with a dehalogenase enzyme.

6. A process as claimed in claim 5 in which the residual hydroalkanoic acid is decomposed in a process as claimed in claim 1.

7. A process as claimed in claim 1 in which the enzyme is a dehydrohalogenase.

8. A composition which comprises a surfactant, thioglycollic acid or carboxymethyl cellulose and a dehalogenase enzyme in an amount sufficient substantially to reduce the concentration of a haloalkanoic acid initially present in said composition, wherein said haloalkanoic acid is chloroacetic acid or chloropropionic acid.

9. A process as claimed in claim 1 in which the surfactant is of formula $R(AO)_n$ OZ COOH in which AO is an ethylene oxide and/or propylene oxide residue, R is an alkylphenyl or alkyl group having 8 to 20 carbon atoms, n has a value of 1½ to 20 and n is an average value and Z is an alkylene group having 1 to 4 carbon atoms.

10. A composition as claimed in claim 8 in which the surfactant is of formula $R(AO)_n$ OZ COOH in which AO is an ethylene oxide and/or propylene oxide residue, R is an alkylphenyl or alkyl group having 8 to 20 carbon atoms, n has a value of 1½ to 20 and n is an average value and Z is an alkylene group having 1 to 4 carbon atoms.

* * * * *